United States Patent
Grollier et al.

(10) Patent No.: US 6,177,100 B1
(45) Date of Patent: Jan. 23, 2001

(54) COSMETIC OR PHARMACEUTICAL COMPOSITION FOR THE TREATMENT OF THE HAIR AND SCALP

(75) Inventors: Jean-François Grollier; Isabelle Hansenne-Richoux, both of Paris (FR)

(73) Assignee: L'Oreal, Paris (FR)

( * ) Notice: Under 35 U.S.C. 154(b), the term of this patent shall be extended for 0 days.

(21) Appl. No.: 09/277,765

(22) Filed: Mar. 29, 1999

Related U.S. Application Data

(63) Continuation of application No. 08/068,666, filed on May 28, 1993, now abandoned, which is a continuation-in-part of application No. 07/443,396, filed on Nov. 30, 1989, now abandoned.

(30) Foreign Application Priority Data

Dec. 2, 1988 (LU) ........................................................ 87.399

(51) Int. Cl.$^7$ ................ A61K 7/00; A61K 7/06; A61K 9/127
(52) U.S. Cl. ................ 424/450; 424/401; 424/404; 424/59; 424/70.1; 514/725; 514/844; 514/880; 514/937
(58) Field of Search ..................................... 424/401, 450, 424/59, 70.1, 404; 514/725, 844, 880, 937

(56) References Cited

U.S. PATENT DOCUMENTS

| | | | |
|---|---|---|---|
| 4,772,471 | * | 9/1988 | Vanlerberghe ........................ 424/450 |
| 4,830,857 | | 5/1989 | Handjani . |

FOREIGN PATENT DOCUMENTS

| | | |
|---|---|---|
| 0 138 395 | 4/1985 | (EP) . |
| 2157168 | * 10/1985 | (GB) . |
| 2 157 168 | 10/1985 | (GB) . |
| 6 019 710 | 7/1983 | (JP) . |
| 6 363 606 | 9/1986 | (JP) . |
| 6 323 0620 | 9/1988 | (JP) . |
| 63-230620 | * 9/1988 | (JP) . |
| 8 806 881 | 9/1988 | (WO) . |

* cited by examiner

Primary Examiner—Gollamudi S. Kishore
(74) Attorney, Agent, or Firm—Nixon & Vanderhye P.C.

(57) ABSTRACT

A cosmetic or pharmaceutical composition for the treatment of the hair and scalp contains nonionic lipids capable of forming a lipidic lamellar phase in combination with an aqueous solution containing at least one cationic surface active agent and/or a quaternized protein.

17 Claims, No Drawings

COSMETIC OR PHARMACEUTICAL COMPOSITION FOR THE TREATMENT OF THE HAIR AND SCALP

This application is a continuation of Ser. No. 08/068,666 filed May 28, 1993, now abandoned, which is continuation-in-part of application Ser. No. 07/443,396 filed Nov. 30, 1989 now abandoned.

The present invention relates to a cosmetic or pharmaceutical composition for the treatment of the hair and scalp.

It is well known that hair is, to various degrees, sensitized or made brittle by the action of atmospheric agents, as well as by the action of various cosmetic treatments such as permanent waving, dyeing or bleaching. The hair then becomes difficult to disentangle and to style. Moreover, the hair becomes harsh to the touch.

Compositions have been sought which facilitate disentangling and styling of the hair and improve its softness to the touch. To this end, cationic surface active agents are currently employed. While these surface active agents improve the disentangling and styling of the hair, they exhibit some disadvantages: they have a tendency to make the hair heavy and impart to it an oily appearance. These disadvantages are all the more accentuated as the hair being treated is more fine.

To this same end, the use of quaternized proteins has been proposed. These proteins neither make the hair heavy nor impart an oily appearance to it. To the contrary, while they improve disentangling and styling of the hair they are clearly inferior in these respects to the results achieved by cationic surface active agents.

Attempts have also been made to use compositions containing both a cationic surface active agent and a quaternized protein. But in this case, the effect obtained is inferior to the sum of the effects that are obtained separately with the use of the cationic surface active agent and the use of the quaternized protein. In the majority of the cases, the presence of the cationic surface active agent on the hair interferes with the quaternized protein.

Moreover, it has been known for a very long time to use oils and fatty bodies to restore softness and shine to the hair. The application of these compounds is generally followed by a shampoo to eliminate from the hair excess oil or fatty bodies. However, the use of oils and fatty bodies weakens the hair and makes it heavy, and it is impossible subsequently to obtain a style having hold and volume.

GB-A 2 157 168 proposes to combine in a composition at least one cationic surface active agent, at least one water soluble quaternized protein and at least one cationic silicon polymer so as to obtain compositions which easily permit disentanglement and styling of the hair without weakening the hair and which impart to the hair shine and softness. Moreover, after disentanglement, the hair is supple and light from the roots to the tips, even in the case of sensitized hair.

According to the present invention, it has now been found that, by replacing the silicon polymer in the above-mentioned compositions with hydrated lipids, the resulting composition exhibits effects which are at least equivalent to and more often better than those obtained with the corresponding compositions containing the cationic silicon polymers, especially with respect to the lightness and the fullness of the treated hair. Moreover, compositions obtained with non-ionic amphiphilic lipids surprisingly provide the advantage of exhibiting a hydrating effect on the scalp, in absence of any hydrating agent. This effect provides an agreeable sensation of freshness and comfort to the scalp during application of the compositions to the scalp. It results from these facts that the compositions according to the invention do not contain cationic silicon polymers.

Moreover, the compositions in accordance with the present invention have excellent storage stability.

The present invention thus relates to a cosmetic or pharmaceutical composition for the treatment of the hair and scalp comprising non-ionic amphiphilic lipids capable of forming a hydrated, lipidic lamellar phase, insoluble in water, optionally combined with a stabilizing agent, the said lipids being dispersed in a continuous aqueous phase, wherein said aqueous phase contains:

(1) at least one cationic surface active agent having the formula $$\begin{matrix} R_1 & R_3 \\ & N^{\oplus} \\ R_2 & R_4 \end{matrix} \quad X^{\ominus} \tag{I}$$

wherein

X is principally chloride or $CH_3SO_4^-$ and $R_1$ is $C_1-C_6$ alkyl, preferably, methyl, and in which:

(a) when X is chloride:
  either $R_2$ and $R_3$ are $C_1-C_4$ alkyl, identical or different from $R_1$ and each other, and $R_4$ is $C_{16}-C_{22}$ alkyl;
  or $R_2=R_1$ and, in this case:
    either $R_3=R_4=C_{18}$ alkyl;
    or $R_3=(C_{17}$ alkyl)amidopropyl and $R_4=(C_{14}$ alkyl) acetate;

(b) when X is $CH_3SO_4^-$:
  $R_2$ represents (alkyl and/or alkenyl)amidoethyl, in which the alkyl and/or alkenyl radical is $C_{13}-C_{21}$ and is derived from fatty acids of tallow;
  $R_3$ and $R_4$ together with the nitrogen atom to which they are attached form a substituted 4,5-dihydroxyimidazole heterocycle, principally a 2-($C_{13}-C_{21}$ alkyl derived from the fatty acids of tallow) 4,5-dihydroxyimidazole and/or (2) at least one quaternized protein constituted by a chemically modified polypeptide having, at the extremity or grafted onto it, at least one quaternized ammonium group which contains at least one $C_1-C_{18}$ alkyl group, the polypeptide being selected from among the hydrolyzates of animal protein.

When this hydrated lipidic lamellar phase forms vesicles, they are called niosomes. The niosomes contained in the composition according to the present invention have, advantageously, an average diameter ranging from 0.01 to $5\mu$ and preferably from 0.1 to $0.35\mu$.

The niosomes are known in the art. They, as well as a process for their preparation, are described in FR-A-2315 991, U.S. Pat. No. 4,772,471 and WO-88/06881. They are spherules or vesicles constituted of one or more concentric lipid layers separated by layers of an internal aqueous phase. In the case of niosomes, the lipids employed for the production of the spherules or vesicles are, in a known manner, nonionic amphiphiles, of synthetic or natural origin, having per molecule, one or several long chain hydrocarbons.

In accordance with the invention the nonionic lipidic amphiphile compounds constituting the hydrated, lipidic lamellar phase, insoluble in water, are advantageously selected from the linear or branched ethers or esters of polyglycerol having the respective formulas:

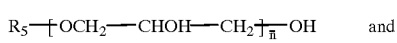

(II)

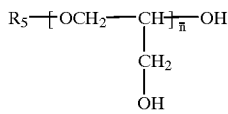

(III)

wherein
$\overline{n}$ has a statistical average value between 2 and 6 and $R_5$ is:
(1) either an $R_6$ aliphatic chain or $R'_6CO$ radical, wherein $R_6$ is a linear or branched aliphatic radical having 12–18 carbon atoms and $R'_6$ is a linear or branched aliphatic radical having 11–17 carbon atoms; or
(2) a

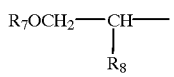

radical wherein $R_7$ and $R_8$, each independently, are $R_6$ and $R'_6$ radicals, $R_6$ and $R'_6$ having the meanings given above.

In a known manner, these nonionic lipidic compounds constituting the hydrated lipidic lamellar phase are, preferably, combined with at least one stabilizing additive so as to modify the permeability or the superficial charge of the lipidic layers of the hydrated lipidic lamellar phase. In accordance with the present invention, the stabilizing additives are more particularly selected from the group consisting of sterols such as cholesterol or β-sitosterol; monosodium or disodium salts of acyl glutamates, the acyl radical having 14–22 carbon atoms, such as the monosodium salt of stearoyl glutamate, the disodium salts of cocoyl glutamate, of stearoyl glutamate or of mixtures of acyl radicals derived from copra and tallow; and phosphoric esters of $C_{12}$–$C_{16}$ fatty alcohols.

In the case where the nonionic amphiphilic lipid is a compound of formula (II) or (III) defined above, where $R_5$ represents $R_6$ or $R'_6CO$, $R_6$ and $R'_6$ having the above-indicated meanings, the said nonionic amphiphilic lipid is combined with both a sterol, preferably cholesterol, and an anionic additive.

The anionic stabilizers are combined with the nonionic amphiphilic lipid compounds in an amount not exceeding 12 percent by weight relative to the weight of the nonionic amphiphilic lipids constituting the hydrated lipidic lamellar phase. For the sterols, and principally cholesterol, this same proportion must remain lower than or equal to 100 percent by weight.

In accordance with the invention, the hydrated lipidic lamellar phase contains water in the presence or not of a cosmetically or pharmaceutically active agent. Representative active agents include, for example, agents combatting hair loss or agents favoring hair growth, retinoids and related compounds, anti-inflammatory agents, anti-fungus agents, anti-seborrheic agents, sunscreen agents and similar products.

The cationic surface active agent present, in accordance with the invention, in the continuous aqueous phase of the composition, is advantageously selected from the group consisting of:
(a) tetraalkylammonium halides such as behenyltrimethyl-ammonium chloride, distearyldimethylammonium chloride, and trimethylcetylammonium chloride;
(b) stearamidopropyldimethyl (myristyl acetate) ammonium chloride having the formula:

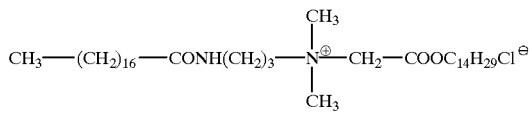

(IV)

such as the product sold under the trade name "CERAPHYL 70'" by the Van Dyk company; and
(c) a quaternary ammonium salt having the formula:

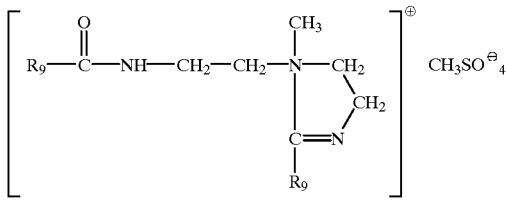

(V)

wherein
$R_9$ represents a mixture of alkenyl and/or alkyl radicals having 13–21 carbon atoms and derived from the fatty acids of tallow, such as the product sold under the trade name "REWOQUAT W 7500" by the "REWO" company.

The quaternized protein contained, in accordance with the invention, in the continuous aqueous phase is advantageously selected from the group consisting of:
(a) certain protein hydrolyzates carrying, on the polypeptidic chain, quaternary ammonium groups having at least one $C_1$–$C_{18}$ alkyl radical and, principally, an animal protein hydrolyzate sold under the trade name "CROTEIN Q" by the Croda company, whose polypeptide chain has an average molecular weight in the order of 12,000;
(b) animal protein hydrolyzates carrying trimethylbenzyl ammonium groups (called "benzyltrimonium hydrolyzed animal protein" in the CTFA Cosmetic Dictionary" (3rd edition, 1982) published by "The Cosmetic Toiletry and Fragrance Association Inc." and hereafter called "CTFA dictionary) and, for example, that sold under the trade name "CROTEIN BTA" by the Croda company;
(c) collagen hydrolyzates having triethylammonium groups, called "Triethonium hydrolysed collagen ethosulfate" in the CTFA dictionary and sold under the trade name "QUAT-PRO E" by the Maybrook company;
(d) collagen hydrolyzates having trimethylammonium and trimethylstearyl ammonium groups, called in the CTFA dictionary, "Steartrimonium hydrolysed collagen" and sold under the trade name "QUAT PRO S" by the Maybrook company; and
(e) a quaternized protein resulting from the condensation of cocamidopropyldimethyl amine on a hydrolyzed animal protein called, in the supplement of the 3rd edition (1982) of the CTFA dictionary, "Cocamidopropyldimonium hydroxypropylamino hydrolyzed animal protein", sold under the trade name "LEKEIN QX 3000'"" by the Inolex company.

The compositions according to the present invention can, preferably, contain both at least one cationic surface active agent and at least one quaternized protein. In this case:

the cationic surface active agent is, preferably, a tetraalkylammonium chloride of formula (I) wherein $R_1$, $R_2$ and $R_3$ are $C_1$–$C_4$ alkyl radicals and $R_4$ is a $C_{20}$–$C_{22}$ alkyl radical; and the quaternized protein is, preferably, an animal protein hydrolyzate having quaternary ammonium groups having a $C_1$–$C_{18}$ alkyl radical.

The continuous aqueous phase of the dispersion can optionally contain, in addition to the cationic surface active agent and/or the quaternized protein, at least one known additive such as a preservative, a stabilizer, a dye, a perfume, a softening agent, a humectant selected preferably from polyols such as glycerine, and thickening agents such as fatty alcohols oxyethylenated or not.

In the composition according to the invention, the cationic surface active agent represents from 0.05 to 10 weight percent, preferably from 0.1 to 6 weight percent, based on the total weight of the composition; the quaternized protein represents from 0.05 to 3 weight percent, preferably from 0.05 to 0.5 weight percent, based on the total weight of the composition; the nonionic amphiphilic lipid, which constitutes the lamellar phase, represents from 0.1 to 20 weight percent, preferably from 1 to 10 weight percent, and more particularly from 3 to 10 weight percent, based on the total weight of the composition.

It is well understood that, in the case where a large amount of cationic surface active agent is employed relative to the nonionic amphiphilic lipid the choice of the cationic agent is not indifferent and must be made in a manner so as not to destroy the vesicles.

The composition according to the invention is generally prepared by mixing two constituents (A) and (B). Constituent (A) contains the hydrated lipidic lamellar phase in a continuous aqueous phase. Constituent (B) contains, in an aqueous phase, the cationic surface active agent and/or the quaternized protein. Each of the constituents can include, moreover, various additives. It is preferred that each of constituents (A) and (B) represents 40 to 60 weight percent relative to the total weight of the composition; advantageously the two constituents being mixed have essentially the same weight.

Constituent (A) is prepared in a conventional manner and more particularly in accordance with procedures described in French patent No. 2 315 991;

in a first stage, the nonionic amphiphilic lipid, optionally admixed with additives so as to modify the permeability or charge of the lipidic layers of the hydrated lipidic lamellar phase it is desired to form, is contacted with water;

in a second stage, an aqueous dispersion phase is added to the resulting hydrated lipidic lamellar phase;

in a third stage, the mixture is vigorously stirred so as to obtain vesicles.

Once constituent (B) is prepared, it is added to constituent (A), with stirring, until complete homogenization.

The compositions according to the present invention are, preferably, applied in the form of products to be rinsed off, before and more particularly after a shampoo, before and more particularly after dyeing or bleaching the hair, before and more particularly after a permanent waving or straightening of the hair. They can also be applied in the form of non-rinsed products, for example, before setting or brushing the hair.

To employ the compositions according to the invention with the view of treating the hair and/or scalp, there is applied to the substrate to be treated an effective amount of the composition according to the invention. The composition is permitted to remain in contact with the substrate for a period of time ranging from 1 to 15 minutes before rinsing off the composition when the composition is one to be rinsed off. The appropriate amount of the composition to be applied to the head is, generally, in the order of 20 to 40 grams in the situation where the product is one to be rinsed off, and in the order of 5 to 10 grams when the product is a non-rinsed product.

The examples below which are purely illustrative and non-limiting, are given to provide a better understanding of the invention.

EXAMPLE 1

In a first stage, constituent (A) comprising vesicles is prepared by dissolving, with gentle stirring, at a temperature of 80° C., a mixture of 6 g of a nonionic lipid having the formula

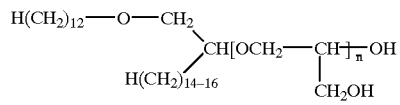

where $\overline{n}$ has an average statistical value equal to 6, with 1.6 g of cholesterol.

The resulting dissolved mixture is introduced into 16 g of water heated to 90° C. and containing a preservative. The mixture is stirred for about 5 minutes. To the resulting phase 24 g of water at 20° C. are added. This mixture is stirred and again 2.3 g of water at 20° C. are added.

In a second step, constituent (B) is prepared by admixing the following B1 and B2 formulations:

| B1 Formulation | |
|---|---|
| 30/70 mixture of cetyl alcohol/ stearyl alcohol | 2.25 g |
| Cetyl alcohol/stearyl alcohol oxyethylenated with 33 moles of ethylene oxide | 0.55 g |
| Octyldodecanol | 0.4 g |
| 50/50 mixture of cetyl alcohol/ stearyl alcohol | 1.2 g |
| B2 Formulation | |
| Glycerine | 0.4 g |
| Behenyltrimethylammonium chloride sold under the trade name "GENAMIN KDM-F" by Hoechst | 3.0 g |
| Protein hydrolyzate, having a polypeptide chain having a molecular weight of about 12,000 and quaternary ammonium groups having at least one $C_1$-$C_{18}$ alkyl group, sold under the trade name "CROTEIN Q" by Croda | 0.25 g |
| Preservative, sufficient amount | |
| Water | 40 g |

The mixture of the B1 and B2 formulations is carried out with stirring which is maintained until the mixture is completely cooled.

In a third step, constituent A and constituent B are mixed together, and the mixture is stirred until it is completely homogenized.

This composition is applied at a rate of about 25 g to the scalp and hair which have been washed and dried. After a contact time of 10 minutes, the hair is rinsed with water. A freshening sensation on application to the scalp is observed. After drying, it is noted that the hair is sheathed and that the style is light and full. The hair is easily disentangled, shiny, soft and supple up to the ends thereof.

EXAMPLE 2

A capillary cream to be rinsed off is prepared by proceeding in accordance with the technique described in Example 1. Constituent A is prepared by gently stirring at a temperature of 80° C. a mixture of 3.8 g of a nonionic lipid having the formula:

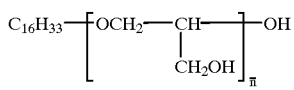

wherein $\bar{n}$ has an average statistical value equal to 3, with 3.8 g of cholesterol and 0.4 g of the monosodium salt of glutamate having the formula

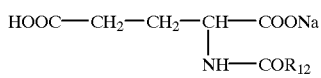

wherein $R_{12}$ is a mixture of hydrogenated alkenyl and/or alkyl radicals having 13–21 carbon atoms derived from the fatty acids of tallow, sold under the trade name: "Acyl-glutamate HS 11" by the Ajinomoto company.

To the resulting dissolved mixture there is added water heated to 90° C. which includes a preservative and the mixture is stirred for a few minutes. To the phase thus obtained, there is added, with stirring, cold water in an amount sufficient to provide 50 g.

Into constituent (A) thus prepared, constituent (B) described in Example 1 is introduced and the mixture is stirred until it is homogenized.

This cream is applied to the scalp and hair previously washed and dried, and it provides the same advantages as those obtained in Example 1.

EXAMPLE 3

The procedures of Example 1 are repeated by using in constituent (B) the following B2 formulation:

| | |
|---|---|
| Glycerine | 0.4 g |
| Collagen hydrolyzate having triethylammonium groups, sold under the trade name "QUAT PRO E" by Maybrook | 1 g |
| Preservative, sufficient amount | |
| Water | 43 g |

This cream is applied to previously washed and dried scalp and hair and it provides the same advantages as those obtained in Example 1.

EXAMPLE 4

Example 1 is reproduced by using in constituent (B) the following B2 formulation:

| | |
|---|---|
| Glycerine | 0.4 g |
| Distearyldimethylammonium chloride | 6 g |
| Preservative, sufficient amount | |
| Water | 38 g |

This cream is applied to previously washed and dried scalp and hair and it provides the same advantages as those obtained in Example 1.

EXAMPLE 5

The procedures of Example 1 are repeated by using in constituent (B) the following B2 formulation:

| | |
|---|---|
| Glycerine | 0.4 g |
| Quaternary ammonium salt, sold under the trade name "REWOQUAT 7500 PG" by Rewo | 5 g |
| Preservative, sufficient amount | |
| Water | 40 g |

This cream is applied to previously washed and dried hair and scalp and it provides the same advantages as those obtained in Example 1.

EXAMPLE 6

A capillary cream, to be rinsed off, is prepared by proceeding in accordance with the technique described in Example 1. Constituent (A) is prepared by gently stirring at a temperature of 80° C. a mixture of 3.8 g of a nonionic amphiphilic lipid having the formula:

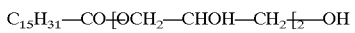

with 3.8 g of cholesterol and 0.4 g of the monosodium salt of glutamate having the formula:

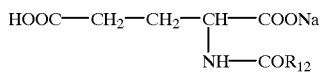

wherein $R_{12}$ is a mixture of hydrogenated alkenyl and/or alkyl radicals having 13–21 carbon atoms derived from the fatty acids of tallow and sold under the trade name "Acyl-glutamate HS 11" by the Ajinomoto company.

To the resulting dissolved mixture water heated to 90° C. and including a preservative is added and the mixture is stirred for a few minutes. To the phase thus obtained cold water is added with stirring in an amount sufficient to provide 50 g.

Into constituent (A) thus prepared, constituent (B) described in Example 1 is introduced and the mixture is stirred until homogenization is achieved.

This cream is applied to previously washed and dried scalp and hair and it provides the same advantages as those obtained in Example 1.

EXAMPLE 7

Example 2 is reproduced except that the 0.4 g of the monosodium salt of glutamate having the formula described in Example 2 is replaced by 0.4 g of sodium dihexadecylphosphate.

A cream is obtained which provides the same effects on the hair as those obtained with the cream obtained in Example 2.

EXAMPLE 8

An antipellicular cream is prepared based on the composition of Example 1 by introducing to the dissolved mixture of lipid and cholesterol, 0.5 g of the ethanolamine salt of 1-hydroxy-4-methyl (2,4,4-trimethyl)-6-pentyl 1H-2-pyridone, sold under the trade name "OCTOPIROX" by Hoechst.

After biweekly applications for 3 months a regression of the number of pellicules is observed.

The cosmetic effect on the hair is the same as that described in Example 1.

EXAMPLE 9

A capillary cream is prepared based on the composition of Example 1, by introducing into the dissolved mixture of the lipid and cholesterol, 0.5 g of a terpenic derivative (BISABOLOL), sold under the trade name "DRAGOSANTOL" by the Dragoco company.

On application of this cream, in particular after a permanent wave, a hair straightening operation or a hair bleaching operation, the user experiences an appeasing sensation on the scalp.

After drying, the hair is sheathed, the style is light and full. The hair easily disentangles, is shiny, soft and supple up to its ends.

EXAMPLE 10

A capillary cream is prepared based on the composition of Example 1, by introducing in the 16 g of water heated to 90° C. and containing a preservative, 3 g of a hydrating agent sold under the trade name "PRODEW 100" by the Ajinomoto company.

During application a hydrating effect on the scalp is obtained.

The same advantages on the hair as those described in Example 1 are also achieved.

EXAMPLE 11

A capillary fluid is prepared in accordance with the procedures described in Example 1.

The constituent (A) is prepared by mixing at a temperature of 80° C., 3.8 g of the nonionic amphiphilic lipid described in Example 2, with 3.8 g of cholesterol and 0.4 g of sodium dihexadecyl phosphate. Thereafter the procedures indicated in Example 2 are followed.

Constituent (B) is then added to the above prepared constituent (A).

Constituent (B) has the following formulation:

| | | |
|---|---|---|
| Constituent $B_1$: identical to that of Example 1 | | |
| Constituent $B_2$: | | |
| Behenyltrimethylammonium chloride, sold under the trade name "GENAMIN KDM-F" by Hoechst | 3.125 g | |
| Honey of acacia, sold by Mellitag | 0.5 g | |
| Preservative, sufficient amount | | |
| Water | 40 g | |

The composition is applied to the scalp and hair as indicated in Example 1 and it provides the same advantages.

EXAMPLE 12

A capillary fluid is prepared in accordance with the procedures set forth in Example 1.

Constituent (A) is identical to that described in Example 1.

Constituent (B) has the following formulation:

| | | |
|---|---|---|
| $B_1$: | identical to that described in Example 1 | |
| $B_2$: | proteinhydrolyzate, having a polypeptide chain, having a molecular weight of about 12,000 and quaternary ammonium groups having at least one $C_1$-$C_{18}$ alkyl group, sold under the trade name "CROTEIN Q" by Croda | 0.25 g |
| | Honey of acacia, sold by Mellitag | 0.5 g |
| | Preservative, sufficient amount | |
| | Water | 40 g |

This composition is applied to the scalp and hair under the same conditions as those set forth in Example 1 and it provides the same advantages.

EXAMPLE 13

A capillary fluid is prepared in accordance with the procedures described in Example 1.

Constituent (A) is identical to that of Example 1

Constituent (B) has the following formulation:

| | | |
|---|---|---|
| $B_1$: | identical to that described in Example 1 | |
| $B_2$: | Behenyltrimethylammonium chloride, sold under the trade name "GENAMIN KDM-F" by Hoechst | 3.125 g |
| | Quaternized collagenic protein hydrolyzate, sold under the trade name "CROTEIN Q" by Croda | 0.25 g |
| | Honey of acacia, sold by Mellitag | 0.5 g |
| | Preservative, sufficient amount | |
| | Water | 40 g |

This composition is applied to the scalp and hair under the same conditions as those set forth in Example 1 and it provides the same advantages.

We claim:

1. A cosmetic or pharmaceutical composition for the treatment of the hair and scalp consisting essentially of a continuous aqueous phase containing vesicles and at least one of a cationic surface active agent and a quaternized protein, said vesicles consisting essentially of a non-ionic amphiphilic lipid material which form a hydrated lipidic lamellar phase in the form of said vesicles, which are insoluble in water, said nonionic amphiphilic lipid material being selected from the group consisting of linear or branched ethers or esters of polyglycerol having the respective formulas (II) and (III):

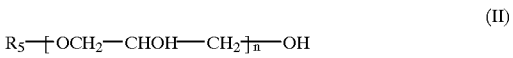

(II)

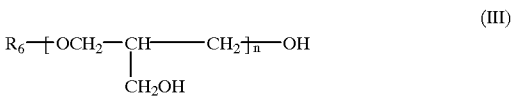

(III)

wherein
n ha statistical average value between 2 and 6 and
R$_5$ is:
either (1) an R$_6$ aliphatic chain or R'$_6$ or R$_6$CO radical, R$_6$ being a linear or branched aliphatic radical having 11–17 carbon atoms or (2) a radical

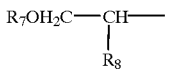

wherein R$_7$ and R$_8$ are R$_6$ or R'$_6$ radicals, identical or different, R$_6$ and R'$_6$ having the meanings given above, said nonionic amphiphilic lipid material being present in an amount ranging from 0.1 to 20 weight percent based on the total weight of said composition; said at least one cationic surface active agent having the formula:

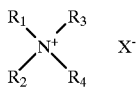

(I)

wherein
X is chloride or CH$_3$SO$^\ominus_4$ and R$_1$ is a C$_1$–C$_4$ alkyl radical and in which;
(a) when X is chloride:
  either R$_2$ and R$_3$ are C$_1$–C$_4$ alkyl radicals, identical or different from R$_1$ and each other, and R$_4$ is C$_{16}$–C$_{22}$ alkyl radical;
  or R$_2$=R$_1$ and, in this case:
  either R$_3$=R$_4$=C$_{18}$ alkyl;
  or R$_3$=(C$_{17}$ alkyl)amidopropyl aid R$_4$=(C$_{14}$ alkyl) acetate and
(b) when X is CH$_3$SO$^\ominus_4$:
  R$_2$ represents a radical selected from the group consisting of an alkyl alkenyl amidoethyl radical and an alkenyl amidoethyl radical, in which the alkyl and alkenyl radical contains 13–21 carbon atoms and is derived from fatty acids of tallow, and
  R$_3$ and R$_4$ together with the nitrogen atom to which they are attached form a substituted 4,5-dihydroxyimidazol ring substituted in position 2, said cationic surface active agent being present in an amount ranging from 0.05 to 10 weight percent based on the total weight of said composition; and
  said at least one quaternized protein constituted by a chemically modified polypeptide having at least one quaternary ammonium group having at least one C$_1$–C$_{18}$ alkyl chain, the polypeptide being selected from the hydrolyzates of animal protein, said quaternized protein being present in an amount ranging 0.05 to 3 weight percent based on the total weight of said composition;
  wherein said dispersion is formed by a process comprising preparing, separately, composition of said vesicles in a continuous phase and a composition of an aqueous phase containing said at least one of a cationic surface active agent and a quaternized protein, and mixing said composition of vesicles and said composition of an aqueous phase such that said vesicles are dispersed in said continuous phase containing at least one of said cationic surface active agent and said quaternized protein.

2. The composition of claim 1 wherein said vesicles have an average diameter ranging from 0.01 to 5μ.

3. The composition of claim 1 wherein said vesicles have an average diameter ranging from 0.1 to 0.35μ.

4. The composition of claim 1 wherein said nonionic amphiphilic lipid which constitutes the hydrated lipidic lamellar phase of the vesicles is combined with at least one stabilizing agent selected from the group consisting of a sterol, a monosodium salt of an acylglutamate wherein the acyl moiety has 14–22 carbon atoms, a disodium salt of an acylglutamate wherein the acyl moiety has 14–22 carbon atoms and a phosphoric ester of a C$_{12}$–C$_{18}$ fatty alcohol.

5. The composition of claim 1 wherein said nonionic amphiphilic lipid which constitutes the hydrated lipidic lamellar phase of the vesicles is combined with at least one anionic stabilizing agent in an amount at most equal to 12 weight percent and/or at least one sterol in an amount at most equal to 100 weight percent, the amount being calculated, in both cases, relative to the weight of said nonionic amphiphilic lipid.

6. The composition of claim 1 wherein said nonionic amphiphilic lipid which constitutes the hydrated lipidic lamellar phase of the vesicles comprises an ether or ester of polyglycerol of formula (II) or (III) wherein R$_5$ is an aliphatic chain R$_6$ or R'$_6$CO wherein R$_6$ and R'$_6$ have the meanings given in claim 1 and wherein said nonionic amphiphilic lipid is combined with both a sterol and an anionic stabilizing agent.

7. The composition of claim 1 wherein said hydrated lipidic lamellar phase contains water in the presence of a cosmetically or pharmaceutically active agent.

8. The composition of claim 1 wherein said hydrated lipidic lamellar phase contains water in the presence of a cosmetically or pharmaceutically active agent.

9. The composition of claim 1 wherein said active agent is an agent to combat hair loss, an agent to promote hair growth, a retinoid, a retinoid derivative, an anti-inflammatory agent, an anti-fungus agent, anti-seborrheic agent or a sunscreen agent.

10. The composition of claim 1 wherein said cationic surface active agent contained in the continuous aqueous phase is selected from the group consisting of
(a) a tetraalkylammonium halide,
(b) stearylamidopropyldimethyl (myristyl acetate) ammonium chloride having the formula

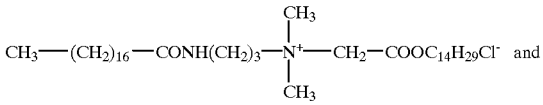

(c) a quaternary ammonium salt having the formula:

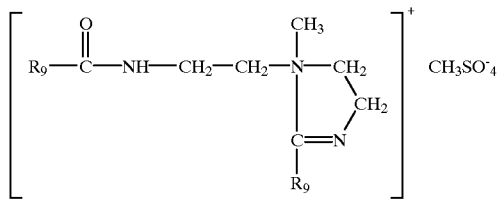

wherein R$_9$ represents a mixture of alkenyl and/or alkyl radicals having 13–21 carbon atoms and derived from the fatty acids of tallow.

11. The composition of claim 1 wherein said quaternized protein is selected from the group consisting of:
(a) animal protein hydrolyzate having on the polypeptide chain quaternary ammonium groups having at least one C$_1$–C$_{18}$ alkyl radical, (b) animal protein hydrolyzates having trimethylbenzylammonium groups, (c) collagen hydrolyzates having trimethylammonium groups, (d) collagen hydrolyzates having trimethylammonium and trimethylstearylammonium groups, and (e) a quaternized protein resulting from the condensation of cocamidopropyldimethylamine on a hydrolyzed animal protein.

12. The composition of claim 1 wherein said cationic surface active agent is behenyltrimethylammonium chloride and said quaternized protein is a hydrolyzate of an animal protein having on the polypeptide chain quaternary ammonium groups having at least one $C_1$–$C_{10}$ alkyl group, the polypeptide chain having an average molecular weight of about 12,000.

13. The composition of claim 1 wherein said continuous aqueous phase contains at least one additive selected from the group consisting of a preservative, a stabilizing agent, a dye, a humectant, a softening agent, a perfume and a thickening agent.

14. The composition of claim 1 containing at least one cationic surface active agent present in an amount ranging from 0.1 to 6 weight percent based on the total weight of said composition.

15. The composition of claim 1 containing at least one quaternized protein present in an amount ranging from 0.05 to 0.5 weight percent based on the total weight of said composition.

16. A process for the treatment of the hair and scalp comprising applying to the hair and scalp 20 to 40 grams of the composition of claim 1, permitting said composition to remain in contact with the hair and scalp for a period of time ranging from 1 to 15 minutes and rinsing the hair and scalp with water.

17. A process for the treatment of the hair and scalp comprising applying to the hair and scalp 5 to 10 grams of the composition of claim 1.

* * * * *